United States Patent [19]

Ogura et al.

[11] Patent Number: 4,484,475
[45] Date of Patent: Nov. 27, 1984

[54] METHOD OF MEASURING CONTACT STRESS AT CONTACTING SURFACES OF ABUTTING SOLID MASSES

[75] Inventors: Yukio Ogura, Chiyodamura; Takeshi Miyajima, Makabemachi, both of Japan

[73] Assignee: Hitachi Construction Machinery Co., Ltd., Tokyo, Japan

[21] Appl. No.: 444,391

[22] PCT Filed: Mar. 30, 1982

[86] PCT No.: PCT/JP82/00087
§ 371 Date: Nov. 9, 1982
§ 102(e) Date: Nov. 9, 1982

[87] PCT Pub. No.: WO82/03672
PCT Pub. Date: Oct. 28, 1982

[51] Int. Cl.³ ............................................. G01N 29/00
[52] U.S. Cl. ........................................ 73/579; 73/778
[58] Field of Search .............. 73/572, 579, 582, 580, 73/599, 622, 637, 638, 761, 778

[56] References Cited

U.S. PATENT DOCUMENTS 3,531,982 10/1970 Clotfelter et al. ............... 73/582

FOREIGN PATENT DOCUMENTS 53-143292 12/1978 Japan .

*Primary Examiner*—Anthony V. Ciarlante
*Attorney, Agent, or Firm*—Wenderoth, Lind & Ponack

[57] ABSTRACT

A method of measuring a contact stress at contacting surfaces of solid masses of a same kind or different kinds by utilizing an ultrasonic wave, including the steps of causing an ultrasonic wave to impinge onto the contacting surfaces; comparing an acoustic wave of the ultrasonic wave reflected from the contacting surfaces with an acoustic wave of the ultrasonic wave transmitted through the contacting surfaces (4); and measuring the contact stress using the value of the comparison as the index of evaluation, whereby measuring non-destructively, easily, quantitatively and with a high precision, the contact stress of the contacting surfaces of parts or members constituting, for example, a machine or equipment in their stationary as well as dynamic conditions.

11 Claims, 26 Drawing Figures

Distance from center of left-side bolt to center of sensor (L) mm

METHOD OF MEASURING CONTACT STRESS AT CONTACTING SURFACES OF ABUTTING SOLID MASSES

TECHNICAL FIELD OF THE INVENTION

The present invention concerns a method of measuring the contact stress at contacting surfaces of abutting solid masses of either a same kind or different kinds by utilizing an ultrasonic wave.

The term "contacting surfaces of abutting solid masses" herein used means the contacting surfaces between parts or members constituting an apparatus such as a machine or an architectural structure, used in various industrial fields. This term includes not only the contacting surfaces of abutting solid masses which are stationary, but also those contacting surfaces of abutting solid masses which are in the state of undergoing a relative displacement such as by sliding. Also, the word "solid mass" herein referred to points to a mass of a metal as well as a mass of a non-metal such as glass, ceramic, concrete, synthetic resin, rubber and wood, through which ultrasonic waves can be transmitted.

The types of contact stresses at the contacting surfaces of abutting solid masses referred to above which are the objectives of the technique of the present invention include: the contact stress at the fitting surfaces produced from interference fit due, for example, to shrink fitting, expansion fitting or press-fitting; the contact stress at the die-fastened surfaces on a press; the contact stress at bolt-fastened surfaces; the contact stress at the meshing surfaces of toothed wheels; the contact stress at screwed surfaces; the contact stress between a spline or key and a part or member contacting it; the contact stress between a bearing and a shaft; the contact stress between a valve and a valve seat; the contact stress between a cylinder bore and a piston ring; and other contact stresses at the contacting surfaces between parts or members constituting various apparatuses. The present invention relates to the method of measuring these contact stresses.

BACKGROUND ART

Among the various techniques to which the present invention can be applied, the interference fitting technique which is applicable to shrink fitting, expansion fitting and press-fitting, and which represents a typical method of combining together solid masses of mainly cylindrical configurations, is widely utilized as a means of mechanically combining two parts together. In utilizing this technique, the acquisition of the knowledge of the contact stress at the contacting surfaces of two abutting parts to serve as a measure for determining the degree of interference fit is a matter indispensable for knowing the functioning as well as the mechanical strength of a machine, or for knowing the degree of the true interference fit of combined portions of parts. Heretofore, however, there has not been established a method of directly and quantitatively measuring the contact stress at the contacting surfaces of combined parts.

For the reasons stated above, various means of measuring contact stresses are being studied. However, generally, there have been known only the method of indirectly measuring a contact stress by making use of photoelasticity, and also the method of directly measuring the contact stress by utilizing a pressure-sensitive sheet.

The method which utilizes photoelasticity is such that a model of contacting surfaces is prepared in advance with a synthetic resin which differs in material from the object whose contact stress is to be measured actually, and evaluation is made based on the fringe patterns formed photoelastically at the contacting portions of the model. Thus, a uniformity of nature or property between the object for measurement and the model is required. However, actual no uniformity cannot be obtained owing to the difference in the material, dimension and configuration between the object and the model. Accordingly, not only does there result a delicate discrepancy in the result of the measurement, but also the measurement is affected by the degree of machining precision of the contacting surfaces of the model, causing changes in the optical property of the contacting surfaces to arise, leading to a difficulty in determining the degree of the fringe patterns. On the other hand, the method utilizing a pressure-sensitive sheet for measuring contact stress of stationary planar surfaces such as bolt-fastened contacting surfaces requires the pressure-sensitive sheet to be inserted in advance between the contacting surfaces before measurement. As a result, the state and the property of the contacting surfaces could change in some way or other. As such, according to this prior method which includes measuring the contact stress by separating the contacting surfaces and then observing the condition of the pressure-sensitive sheet, it is not possible to avoid lowering of the accuracy of measurement, and also it is not possible to perform quantitative measurement either. Not only that, the prior method cannot be utilized in making a measurement of contact stress at the contacting surfaces of an interference fit such as shrink fit, expansion fit or press-fit surfaces. The prior methods stated above invariably are directed only to the measurement of the stationary contact stresses, and have the inconvenience and drawback that they do not permit measurement of the so-called dynamic contact stresses wherein the mutual contacting surfaces are displacing relative to each other.

In order to overcome the problems of the prior techniques as stated above, and to perform a measurement while maintaining the state and the nature or property of the contacting surfaces which are to be measured, research is being conducted as the use of ultrasonic waves in contact stress measurement. (see Non-Destructive Inspection, vol. 25, 10th issue, pp. 669–675).

This latter research involves the known technique in which only the intensity of the reflecting wave of an ultrasonic wave at the contacting surfaces of two abutting metal masses is measured, to thereby measure the contact stress at such surfaces. With the known techniques of processing metal surfaces, it is not possible to manufacture a true planar surface or a true curved surface which is free of surface roughness or windings. Rather, usual contact surfaces are inevitably constructed with two abutting surfaces having surface roughness or windings. Such a contact is microscopically enlarged and shown schematically in FIG. 1. It will be noted therein that the two contact surfaces are comprised of a true contact portion C wherein two metal masses are in direct contact with each other, and a contact portion N wherein the two metal masses are not in direct contact with each other and there is air therebetween. When an ultrasonic wave is directed toward the contacting surfaces, there is a tendency for the intensity of the reflecting wave to become smaller with an increase in the area of the true contact surfaces. This known stress measurement technique makes use of said tendency. In fact, the measurement of contact stress is based on this tendency.

In a concrete method of making a measurement which has been attempted in said research, reference test pieces are used to preliminarily establish the reference relationship between contact stress and intensity of reflecting wave, and using this relationship as a correction curve, quantification of the contact stress on the basis of the reflecting wave intensity measurement value is attempted. It has been reported, however, to the effect that "at the present stage, the accuracy of measurement cannot be said good enough to put the present method to practice".

The above-stated method of measuring the intensity of the reflecting wave of ultrasonic wave at the contacting surfaces in order to determine the contact stress between two abutting metal masses is theoretically possible. According to the research conducted by the present inventors, however, it has been found that this proposed prior technique bears various shortcomings from the practical point of view. More particularly, FIG. 2 is an explanatory illustration showing the manner of measuring the intensity of the reflecting wave at the contacting surfaces. In FIG. 2, I and II represent carbon steel pieces, respectively, for machine structural use. These steel pieces are made of a material labeled S35C (JIS G 4051, but containing 0.32–0.38% of carbon). The metal piece I has a thickness $t_1 = 30$ mm, and the metal piece II has a thickness $t_2 = 20$ mm. An ultrasonic wave sensor 2 is applied to a surface of the metal piece I, and an ultrasonic wave having a frequency of 5 MHz is directed onto the contacting surfaces in a direction normal thereto from the sensor 2. While varying the contact stress $\sigma$ of the metal pieces I and II, the intensity h(dB) of the reflecting wave of the ultrasonic wave is measured by the sensor 2. The result of this measurement is shown by way of a graph in FIG. 3. It should be understood that this measurement was conducted by using an ultrasonic flaw detector of pulse echo type, so that the result of the measurement represents the value indicated in decibels on the Braun tube display screen (CRT) of the apparatus.

As will be noted from FIG. 3, the variation of the intensity of the reflecting wave due to the increase in the contact stress is very small, being about 0.2 dB/kg/mm². Such a magnitude of variation as this constitutes a big obstacle in making a correct quantitative evaluation of the contact stress relative to the intensity of the reflecting wave. Furthermore, as stated above, this method preliminarily establishes a reference relationship between the contact stress and the intensity of reflecting waves, and evaluation is made by comparison between this reference value and the intensity of the reflecting wave which is the result of the measurement. It should be noted, however, that with respect to the external surface of the reference test piece on which the ultrasonic wave sensor is placed and also to the external surface of the object requiring a measurement of the stress at the contacting surfaces thereof, there inevitably exist differences in the shape and roughness of the external surfaces, and a difference in the manner of applying the ultrasonic wave thereonto. These differences directly affect the result of the measurement, causing variance in the result of the measurement, and thus making the quantitative evaluation all the more difficult.

OBJECTS OF THE INVENTION

The present invention has, as its basic object, to provide a method of measuring the contact stress at the contact surfaces of abutting solid masses of a same kind or different kinds by utilizing an ultrasonic wave, which eliminates the abovesaid problems of the prior techniques and which permits an evaluation of the correct value quantitatively and with a high accuracy without altering at all the state of contact at the contact surfaces and the nature or property of such state.

Another object of the present invention is to provide a method of measuring the contact stress of the contacting surfaces of abutting solid masses, which in accordance with a measurement can be made during a very short period of time.

Still another object of the present invention is to provide a method of measuring the contact stress of the contacting surfaces of abutting solid masses, which permits an accurate quantitative evaluation to be made at all times without being affected by such factors as the shape and roughness of the surface of the mass on which an ultrasonic wave sensor is placed even when there is a little difference from the precise position in, for example, the manner of directing the ultrasonic wave sensor toward the contact surfaces.

Further objects of the present invention will become apparent from the following detailed description of the present invention when taken in conjunction with the accompanying drawings.

SUMMARY OF THE INVENTION

The present invention features the technique whereby an ultrasonic wave is caused to impinge onto the contacting surfaces of two abutting solid masses, and both the amplitude of the acoustic pressure (intensity) of said ultrasonic wave reflected from the contacting surfaces and amplitude of the acoustic pressure of the ultrasonic wave transmitted through the contacting surfaces are utilized, for conducting a comparison between these two amplitudes of acoustic pressure thereinafter simply "acoustic pressure" to measure the contact stress at said contacting surfaces.

This feature of the present invention utilizes such nature or property at the contacting surfaces as will be described below. That is, the contacting surfaces of two abutting solid masses, as explained with respect to FIG. 1, are comprised of a true contacting portion C at which the two solid masses are in direct contact with each other, and a contacting portion N in which there is air between the opposing surface portions. Accordingly, as the amount of contact stress becomes greater, the protruding portions at the true contacting portion C will collapse to form progressively more plastic deformations, with the result that the amount of the true contacting portion C will increase, as contrasted by a decrease in the amount of the contacting portion N. This fact gives one the idea that as the contact stress increases the acoustic pressure of the reflecting wave of the ultrasonic wave impinging onto the contacting surfaces of the solid masses gradually diminishes, while conversely the acoustic pressure of the transmitted wave increases progressively, and thus the ratio between these two tends to increase with an increase in the amount of contact stress. In order to further clarify the above-mentioned feature of the present invention, it will be described further concretely by referring to FIG. 4 which is an illustration of the principle of the present invention.

More specifically, in FIG. 4, the ratio B/A between the acoustic pressure B of the reflecting wave at the contacting surfaces 4 and the acoustic pressure A of the incident wave, and the ratio C/A between the acoustic pressure C of the transmitted wave and the acoustic pressure A of the incident wave are given by Formulas (1) and (2), respectively.

$$B/A = 1/f(\sigma) \quad (1),$$

and $$C/A = g(\sigma) \quad (2).$$

Here, $f(\sigma)$ and $g(\sigma)$ represent functions of contact stress ($\sigma$), respectively. $f(\sigma)$ and $g(\sigma)$ both have the tendency to assume a greater value as the contact stress ($\sigma$) becomes greater.

The ratio between Formula (1) and Formula (2), i.e. the ratio between B/A and C/A is thus shown by the following Formula (3):

$$B/A / C/A = B/C = 1/f(\sigma) \cdot g(\sigma) \quad (3).$$

The measuring method of the present invention, as stated above, utilizes the ratio B/C between the acoustic pressure B of the reflecting wave and the acoustic pressure C of the transmitted wave. Accordingly, according to the present invention, as will be apparent from Formula (3), the acoustic pressure A of the incident wave is offset, so that the method of the present invention features that it is not affected directly by the acoustic pressure A of the incident wave during the measurement. Also, B/C is expressed as a function of the product of $f(\sigma)$ and $g(\sigma)$. Accordingly, the value of $1/f(\sigma) \cdot g(\sigma)$ accompanying the variation of the contact stress $\sigma$, i.e. the amount of variation of B/C, is greater than the variation in the ratio B/A, and thus it becomes possible to quantitatively evaluate the contact stress with a high accuracy as compared with the conventional technique which uses B/A as an index for evaluation.

The methods of making a comparison between the acoustic pressure of the reflecting wave coming from said contacting surfaces and the acoustic pressure of the transmitting wave which is transmitted through said contacting surfaces may be roughly divided into the following two types. The first one of these two types uses an ultrasonic wave oscillating transducer and a sensor for receiving the reflecting wave coming from the contacting surfaces both of which are provided on the exposed surface of one of the two abutting solid masses, and also uses a sensor provided on the bottom side of the other one of the solid masses for receiving the transmitted wave, and the signals obtained from said reflecting wave receiving sensor and said transmitting wave receiving sensor are compared with each other. The second type of method provides, on the exposed surface of only one of the two abutting solid masses, an ultrasonic wave oscillating transducer, another transducer (sensor) for receiving the reflecting wave coming from the contacting surfaces and still another transducer (sensor) for receiving the reflecting wave coming from the bottom surface of the other one of the solid masses, so that there are obtained a reflecting wave signal (hereinafter to be referred to as a first reflection wave) from the contacting surfaces, and a transmission-reflection wave (hereinafter to be referred to as a second reflection wave which represents the ultrasonic wave having been transmitted through the contacting surfaces and reflecting at the bottom surface of the other one of the solid masses), and these two signals are compared with each other.

As discussed above, the first type of method permits a quantitative evaluation of the contact stress by increasing the degree of change of the detected value in correspondence with the variation of contact stress. However, the second reflection wave in the second type of method, in fact, is the acoustic pressure of the wave which has passed through the contacting surfaces twice. Accordingly, this second type of method makes it possible to further increase the degree of change in the detection value than in the case of the first type of method, and to thereby be able to make a quantitative evaluation with a still higher accuracy.

The abovesaid first type of method and second type of method may be divided further as follows. That is, the two types of method includes methods in which the incidence of the ultrasonic wave is normal to the contacting surfaces, and methods in which the incident ultrasonic wave impinge the contacting surfaces obliquely.

Also, the most preferred method according to the present invention is said second type of method in which the ultrasonic wave impinges normally on the contacting surfaces. The reason therefor is as follows. In case the incidence of an ultrasonic wave is effected in a direction normal to the contacting surfaces both, the first reflection wave coming from the contacting surfaces, and the second reflection wave which is produced in such way that the portion of the incident ultrasonic wave which is transmitted through the contacting surfaces is reflected at the bottom of the solid mass, will be transmitted out of the solid masses at a same single position. Therefore, the functions of the ultrasonic wave oscillating transmitter, the sensor for detecting the first reflection wave coming from the contacting surfaces and the sensor for detecting the second reflection wave all can be performed concurrently by a single transducer. Thus, the amount of the variation of the detection signals due to any difference in the manner of applying the transmitter and sensors to the surface of one of two masses, and the difference in the state of the mass at the positions at which the transmitter and sensors are applied are eliminated, and it becomes possible to detect a signal indicative of the true contact stress.

BRIEF DESCRIPTION OF THE DRAWINGS

FIGS. 19 and 20 are illustrations showing an example of the application of the present invention to the measurement of the contact stress at bolt-fastened surfaces, in which:

FIG. 19 is a schematic illustration of two bolt-fastened masses and a transducer arrangement for carrying out the measurement method of the invention, and FIG. 20 is a graph showing the distribution of contact stress indicating the result of a measurement performed with the arrangement shown in FIG. 19.

FIGS. 23 and 24 are diagrammatic illustrations showing another method of making continuous measurements of contact stress at contacting surfaces of an object via a liquid, in which:

FIG. 23 is a vertical sectional view thereof, and

FIG. 24 is a sectional view taken along the line Y—Y in FIG. 23.

FIGS. 25 and 26 are block diagrams showing the examples in which the present invention is carried out by using an ultrasonic flaw detector, in which:

FIG. 25 shows the instance of carrying out the method illustrated in FIG. 6, and FIG. 26 shows the instance of carrying out the method illustrated in FIG. 14.

DETAILED DESCRIPTION OF THE PREFERRED EMBODIMENTS

Some preferred embodiments of the present invention will be described hereunder by referring to the accompanying drawings.

FIGS. 6 to 11 show a first embodiment of the present invention.

Figure 5:
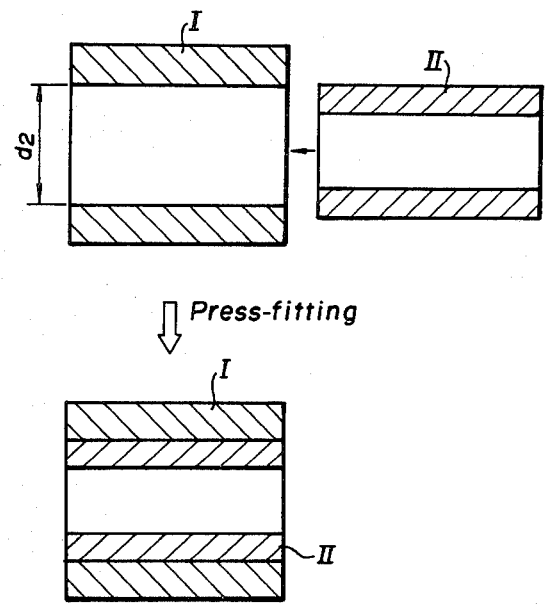
FIG. 5 is a diagrammatic sectional view showing the state of a bushing which is forced into the bore of a boss.

Description will be made first of the instance in which the contact stress at the contacting surfaces of a boss I and a bushing II as illustrated in FIG. 5 is to be measured, by causing an ultrasonic wave to impinge onto the contacting surfaces of these metal masses I and II and comparing the reflection ultrasonic wave reflected at the contacting surfaces with the transmitted ultrasonic wave which has been transmitted through said contacting surfaces.

As a concrete example, there are used an ultrasonic flaw detector 1 of pulse echo type, which is used widely as a testing apparatus for detecting defects in material by utilizing an ultrasonic wave, and its probe 2 (hereinafter to be referred to as an ultrasonic wave transducer. One such sensor is Type SM 90 made by Tokyo Keiki Company, Limited, a Japanese corporation, of Tokyo, Japan. The ultrasonic wave transducer 2 is applied to the outer surface of a metal mass I to emit an ultrasonic wave 3 penetrating into the metal mass I. It should be understood here that the ultrasonic wave transducer used in this embodiment is a longitudinal wave transducer, so that the ultrasonic wave 3 is caused to be emitted in a direction which is substantially normal to the contacting surfaces.

The ultrasonic wave 3 is transmitted through the metal mass I. When the ultrasonic wave 3 reaches the contacting surfaces 4 of the metal masses I and II, a part of the ultrasonic wave 3 is reflected at the contacting surfaces 4, and this reflection wave (hereinafter to be referred to a first reflection wave) 6 comes back to the ultrasonic wave transducer 2. Also, another part of the ultrasonic wave 3 is transmitted through the contacting surfaces 4 and enters the metal mass II. The ultrasonic wave which has entered metal mass II is transmitted through this metal mass II to the bottom surface thereof where it is reflected almost 100%. This new reflected ultrasonic wave is again transmitted through the metal mass II. When this reflection wave arrives at the contacting surfaces 4 of the metal masses II and I, a part of this reflected ultrasonic wave is again reflected at the contacting surfaces 4, whereas the other part thereof is transmitted therethrough. The ultrasonic wave which is transmitted through the contacting surfaces 4 and enters the metal mass I is transmitted through the metal mass I, and comes back to the ultrasonic wave transducer 2 as a post-transmission reflection wave (hereinafter to be referred to as a second reflection wave) 7.

Figure 7:
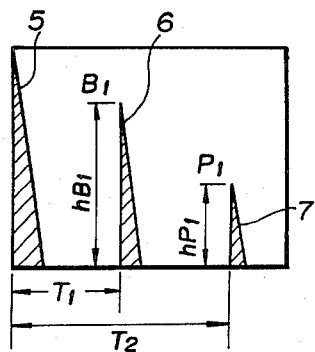
FIG. 7 is an explanatory illustration showing the echo pattern displayed on a CRT, obtained according to the method shown in FIG. 6.

An A-scope which is comprised of an ordinate axis representing the signal reception input supplied from the sensor and an abscissa axis which crosses the ordinate axis at a right angle and representing the transmission time of the ultrasonic wave is displayed on the Braun tube of the ultrasonic flaw detector 1, for observation. The pattern of the $B_1$ echo of the first reflection wave 6 coming from the contacting surfaces and the pattern of the $P_1$ echo of the second reflection wave are as shown in FIG. 7. It will be noted that the $B_1$ echo appears at a position which comes after the lapse of a time $T_1$ corresponding to the thickness $t_1$ of the metal mass I, while the $P_1$ echo appears at a position which comes after the lapse of a time $T_2$ with a delay from the appearance of the $B_1$ echo corresponding to the thickness $t_2$ of the metal mass II.

Figure 1:
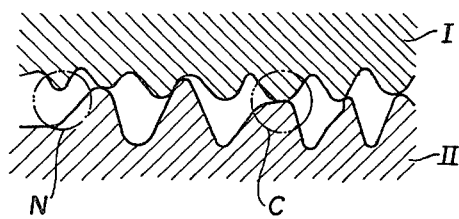
FIG. 1 is a schematic illustration, on a micrographically enlarged scale, showing the state of contact at the contacting surfaces of two metal masses.
Figure 2:
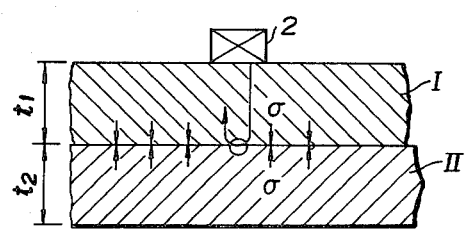
FIG. 2 is a diagrammatic explanatory illustration showing the conventional method of measuring the contacting surfaces by using an ultrasonic wave transducer.

The contacting surfaces of the metal masses I and II are microscopically enlarged and shown schematically in FIG. 1, in which the contacting surfaces are comprised of a true contact portion C, and a contact portion N where metal masses are in direct contact with the intervening air. Therefore, in case the contact stress is small and there is an abundancy of the contact portion N of air and metal mass, upon the application of an ultrasonic wave, the height $h_{B1}$ of the $B_1$ echo will be much greater than the height hP, of the $P_1$, echo, whereas if the contact stress is increased and the amount of the true contact portion C increases, there will be produced an effect that the height $h_{p1}$ of the $P_1$ echo will increase. However, the degree of such proportional effects is subject to a change in surface roughness of the contacting surfaces which is great, and it should be noted that a result more accurate measurement can be obtained from a surface roughness of a smaller degree. In case the surface roughness is very large, it should be noted that even when the plastic deformation of the protrusions present at the opposing contacting surfaces is increased, these surface protrusions are not sufficiently or easily collapsed for such reasons as that the height or pitch of these surface protrusions are great, and as compared with the proportional increase in the contact stress, the proportion of contact portions N to contact portions C will remain large, so that an accurate measurement cannot be obtained. As a result, it can be said that, in case of, for example, a metal mass, the desirable lower limit of surface roughness is about 50 μm. On the other hand, in the prior techniques, measurement of contact stress has relied solely upon the height of $B_1$ echo, as stated above. Therefore, the variation of the height $h_{B1}$ of $B_1$ echo due to the variation of the contact stress is very small, and it has been quite difficult to make a quantitative evaluation of contact stress. According to the present invention, however, it should be noted that, even when the amplitude of the acoustic pressure (intensity) of the incident wave fluctuates owing to the manner of application of the ultrasonic wave sensor, the measurement is not subjected to the effect of the amplitude of such acoustic pressure, and moreover the height $h_{B1}$ of $B_1$ echo and the height $h_{P1}$ of $P_1$ echo are displayed on a same screen so as to allow a comparative reading to be made to thereby enable measurement of the contact stress $\sigma$. Accordingly, there is no need to make a relative comparison with a reference test piece or model, and moreover measurement can be made on the basis of accumulation of the variation of the height of the $B_1$ echo and the variation of the height of the $P_1$ echo resulting from the fluctuation of contact stress. Thus, it is possible to easily make a quantitative evaluation with a high accuracy.

A concrete method of comparison between the $B_1$ echo height $h_{B1}$ and the $P_1$ echo height $h_{P1}$ will be described as follows.

The $B_1$ echo and $P_1$ echo are displayed on a CRT. In case, for example, the height of the $B_1$ echo is 80% on the graduation of the CRT, and the height of the $P_1$ echo is 40%, one typical method seeks the value of comparison $\Delta h$ from the following Formula (4):

$$\Delta h \text{ (dB)} = 20 \log \frac{B_1(\%)}{P_1(\%)} \quad (4)$$

Figure 8:
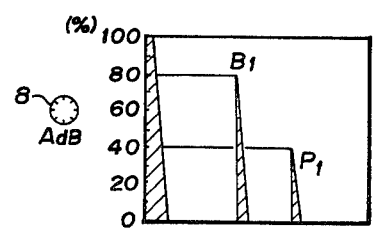
FIGS. 8 and 9 are explanatory illustrations showing an example of the method of comparison between a reflection wave and a transmission wave.
Figure 9:
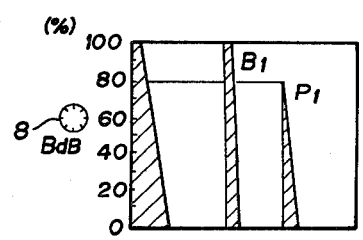

Also, in case of an ultrasonic flaw detector containing a decibel indication amplifier, let us suppose that, at the state shown in, for example, FIG. 8, the knob 8 of the amplifier is A(db). The operator moves the knob 8 from this state to change the height of the $P_1$ echo to the level of 80% on the CRT to a same level as that of the initial $B_1$ echo height shown in FIG. 9. When, thus, the graduation pointed by the knob 8 of the amplifier has become B(db), the comparative value $\Delta h$ will become as shown by the following Formula (5):

$$\Delta h(\text{dB}) = A(\text{dB}) - B(\text{dB}) \quad (5).$$

More specifically, in case the height of echo is indicated in decibels, it becomes possible to very readily obtain the value $\Delta h$ of comparison from the difference in the height of echoes.

In order to obtain the contact stress $\sigma$ directly from the value $\Delta h$ of comparison which has been obtained in a manner as stated above, there is a method in accordance with which an empirical formula which will be stated later is programmed in such means as an electronic computer, and the abovesaid $\Delta h$ and the inner diameter $d_2$ of the boss are inputted for computation of the contact stress. In another method the empirical formula is computed and a chart a graph is prepared therefrom, and the contact stress $\sigma$ is obtained from $\Delta h$ by referring to the chart or graph.

A concrete effect or advantage according to the present invention has been confirmed as a result of the below-described experiments.

Figure 10:
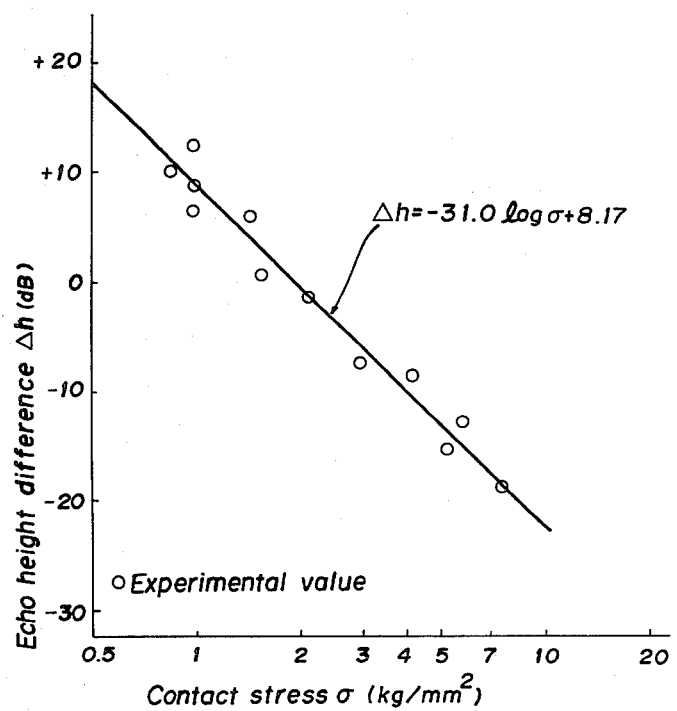
FIG. 10 is a graph showing an example of the relationship between the contact stress obtained by the method illustrated in FIG. 6 and the comparative value of the echo heights.

Employing a longitudinal wave generating sensor which generates an ultrasonic wave of the frequency of 2.25 MHz, and has a vibrating member with a diameter of 10 mm, the relationship between the contact stress produced at the fit surfaces when a bushing II (made of STKM-16A, an induction-hardened steel) is forced into a boss I (made of S35C, a heat refined steel, having an inner diameter of 80 mm) in a manner as shown in FIG. 5 and the comparative value $\Delta h$ of echo height (which means, in this embodiment, the difference in the echo heights expressed in decibels, and therefore to be referred to hereinafter as the echo height difference) was experimentally determined to be as plotted by small circles in FIG. 10. This relationship between the contact stress $\sigma$ and the echo height difference $\Delta h$ shows a change which is by far greater than the variation in the intensity of the reflection wave relative to the increase in the amount of the contact strsss $\sigma$ shown in FIG. 3. Thus, it is noted that there can be made a quantitative measurement with good accuracy.

Based on the values obtained by experiments conducted as above, a regression formula $\Delta h = a \log \sigma + b$ was sought by relying on the least square method, wherein a and b are:

$$a = \frac{n\Sigma\sigma \cdot \Delta h - \Sigma\sigma \cdot \Sigma\Delta h}{n\Sigma\sigma^2 - (\Sigma\sigma)^2},$$

and $$b = \frac{\Sigma\Delta h \Sigma\sigma^2 - \Sigma\sigma \cdot \Sigma\sigma\Delta h}{n\Sigma\sigma^2 - (\Sigma\sigma)^2},$$

wherein: n represents the number of samplings taken in the experiment, and in this case, n=12.

The constants a and b were calculated to be: a=−31.0, and b=8.17. Accordingly, the regression formula is:

$$\Delta h = -31 \log \sigma + 8.17 \quad (6),$$

and the focus of points defined by this formula forms the rectilinear line shown in FIG. 10. As such, between the contact stress $\sigma$ and the echo height difference $\Delta h$, there is established a rectilinear logarithmic correlation as shown in FIG. 10. By using this regression line, it is possible to directly and readily know the contact stress $\sigma$ from the echo height difference $\Delta h$.

Figure 3:
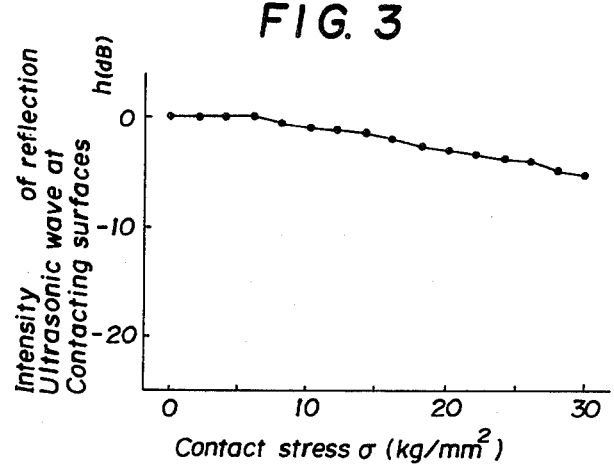
FIG. 3 is a graph showing the relationship between the contact stress and the intensity of the reflecting wave of an ultrasonic wave, obtained by the conventional method shown in FIG. 2.
Figure 4:
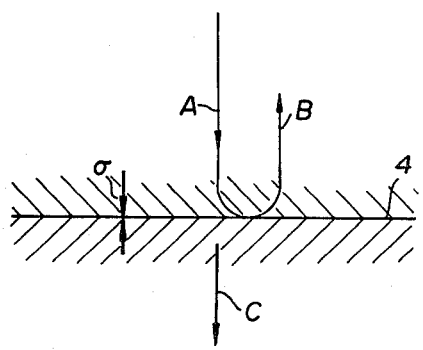
FIG. 4 is an explanatory illustration of the basic principle of the measuring method according to the present invention.

The Regression Formula (3) shown in FIG. 3 represents the result of experiment when the bore diameter $d_2$ of the boss of FIG. 5 was set at 80 mm. It should be understood, however, that in case the bore diameter $d_2$ of a boss of the same material is varied, the Regression Formula will vary accordingly. Therefore, based on the result of experiment which was conducted by varying the bore diameter $d_2$ of the boss, respective regression formulas for the respective bore diameters $d_2$ were obtained by relying on said least square method, and the result was that, as a general formula for $\Delta h$ for a boss of said material, the following Formula (7) was obtained:

$$\Delta h = (49.83 \log d_2 - 126.2) \log \sigma + 33.55 \log d_2 - 55.7 \quad (7)$$

Accordingly, in case the bore diameter $d_2$ of the boss is already known, or in case it is measured by using, for example, a scale, it becomes possible to measure the contact stress from said Formula (7).

Figure 11:
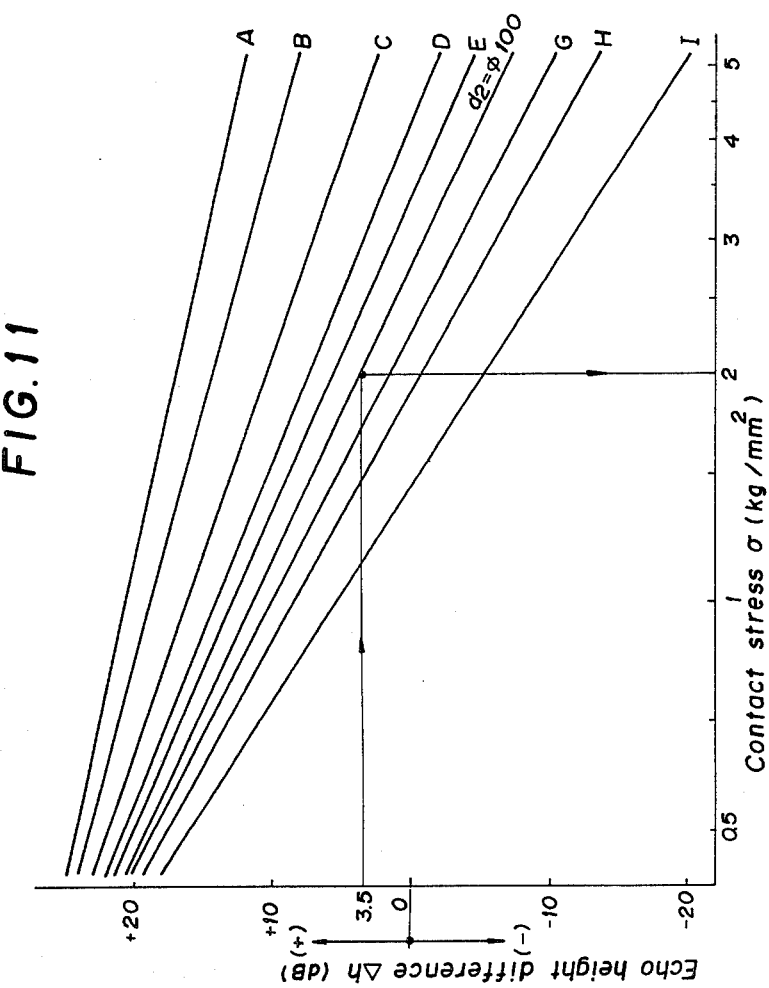
FIG. 11 is a graph showing the relationship between the contact stress and the comparative value of echo height when the inner diameter of the boss is varied.

FIG. 11 shows the relationship between the contact stress $\sigma$ (kg/mm$^2$) and the echo height difference $\Delta h$ for respective bore diameters $d_2$ of the boss shown in FIG. 5, in a manner as described above. By using this graph of FIG. 11, it is possible to readily and directly know the values in such manner that, if, for example, $d_2 = 100$ mm, and if $\Delta h = 3.5$ dB, a perpendicular line is drawn downwardly from the cross point of the horizontal line of 3.5 dB and the line of $d_2 = 100$ mm, to thereby know that $\sigma = 2.0$ kg/mm$^2$.

Also, said Formula (7) may be replaced by:

$$\Delta h = (\alpha \log d_2 - \beta) \log \sigma + \gamma \log d_2 - \delta \quad (8),$$

in which: the constants $\alpha$, $\beta$, $\gamma$, and $\delta$ are determined by the acoustic characteristics of the materials with which the boss and the bushing are made. By preliminarily obtaining the values of $\alpha$, $\beta$, $\gamma$, and $\delta$ for combinations of various kinds of solid masses at the time of experiments, it becomes possible to very easily and directly know the contact stress at fitting surfaces in a manner similar to that described above.

In the above-described embodiment, the ultrasonic wave oscillating transducer concurrently serves as a sensor for the reception of the first reflection wave coming from the contacting surfaces, and also a sensor for the reception of the second reflection wave reflected at the bottom surface of the solid mass after having passed through the contacting surfaces. It should be noted, therefore, that, even if there is some small difference in the manner of application of the ultrasonic wave oscillating transducer to the external surface of the object, the errors arising in the values of detection due to such difference in the manner of application of the transducers are all cancelled out, and it is possible to detect the correct value of $\Delta h$ corresponding to the actual contact stress. This is a fact which is extremely important in actually making a measurement. More particularly, the transducer of an ultrasonic testing apparatus usually is applied to a surface of a metal mass which is coated with an oil or water. However, owing to the condition of coating of oil or water, or to the relative angle between the surface of the sensor and the surface of the metal mass, there could arise a change in the waveshape or height (pitch) of the echo which is obtained. Accordingly, even a same operator is not always able to apply the sensor to the surface of a metal mass in the same fashion every time. However, because the abovesaid embodiment is such that a transducer (transmitter) for emitting an ultrasonic wave, another transducer (sensor) for the reception of the first reflection wave coming from the contacting surfaces, and still another transducer (sensor) for the reception of the second reflection wave which is emitted from the bottom surface after having once passed through the contacting surfaces are concurrently served by a single transducer, there can be obtained a correct value of the echo height difference $\Delta h$ corresponding only to the contact stress at the contacting surfaces.

Description has been made above of an embodiment wherein an ultrasonic wave is directed normally of the contacting surfaces, and wherein both the transmitting sensor and the receiving sensor are served concurrently by a single transducer. It should be understood, however, that the present invention is not limited to such embodiment alone.

Figure 12:
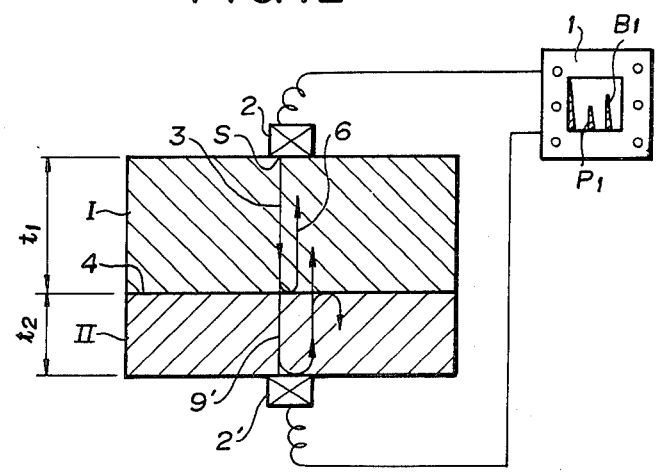
FIGS. 12 to 14 are diagrammatic brief explanatory illustrations similar to FIG. 6 showing other examples of the measuring method of the present invention.

More specifically, FIG. 12 provides a modified arrangement wherein an ultrasonic wave (longitudinal wave) transducer 2 is disposed in such a manner as to insure that an ultrasonic wave 3 impinges onto the surface of the metal mass I in a direction normal to the contacting surfaces 4, and that a transmitted wave reception sensor 2' is disposed on the bottom surface of the metal mass II, so that the $P_1$ echo of the transmitted wave 9 which has been transmitted through the contacting surfaces 4 is detected by the sensor 2', and that the reflection wave 6 which has been reflected from the contacting surfaces 4 is detected by the transducer 2.

Figure 13:
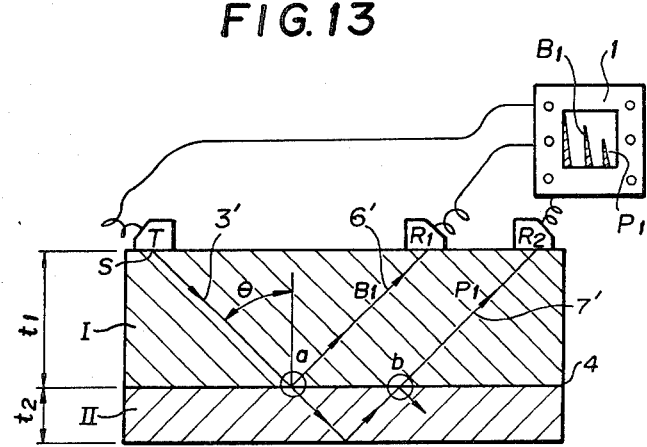
Figure 14:
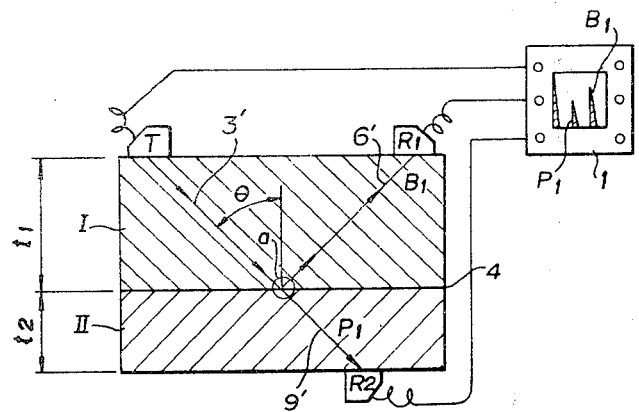

Also, FIGS. 13 and 14 show an example in which transversal wave transducers T, $R_1$ and $R_2$ having an incidence angle $\theta = 45°$ are arranged so that an ultrasonic wave is caused to impinge onto the contacting surfaces 4 of the metal masses I and II at an oblique angle and to be reflected at an oblique angle also.

More particularly, FIG. 13 provides the arrangement that the respective transducers T, $R_1$ and $R_2$ are disposed at the surface of the metal mass I so that an ultrasonic wave 3' is caused to impinge from the transducer T onto the contacting surfaces 4 at an angle of 45° and that the first reflection wave 6' which is reflected at point a of the contacting surfaces 4 is detected by the transducer sensor $R_1$, and that the second reflection wave 7' which is the portion of the ultrasonic wave is transmitted through the point a is reflected at the bottom surface of the metal mass II and then transmitted through point b of the contacting surfaces 4 is detected by the transducer sensor $R_1$, and also that the transmitted wave 9' which has been transmitted through the contacting surfaces 4 is detected by the transducer sensor $R_2$.

The embodiments shown in FIGS. 13 and 14 may be utilized in such cases wherein it is not possible to cause an ultrasonic wave to impinge onto the contacting surfaces in a direction normal thereto, e.g. where there is present any obstacle just above the point of measurement, or the contact stress of the meshing surfaces of toothed wheels is to be measured.

Figure 15:
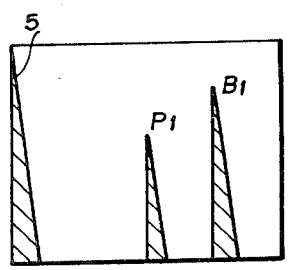
FIG. 15 is an explanatory illustration showing the echo pattern displayed on a CRT, obtained by the methods shown in FIGS. 12 and 14.

In the abovesaid embodiments shown in FIG. 12 and FIG. 14, the position at which the $B_1$ echo of the wave reflected from the contacting surfaces appears and the position at which the $P_1$ echo of the wave which has been transmitted through the contacting surfaces appears are as shown in FIG. 15, and as illustrated therein, the $P_1$ echo appears prior to the appearance of the $B_1$ echo. This is due to the fact that the thickness $t_1$ of the metal mass I is greater than the thickness $t_2$ of the metal mass II.

Figure 16:
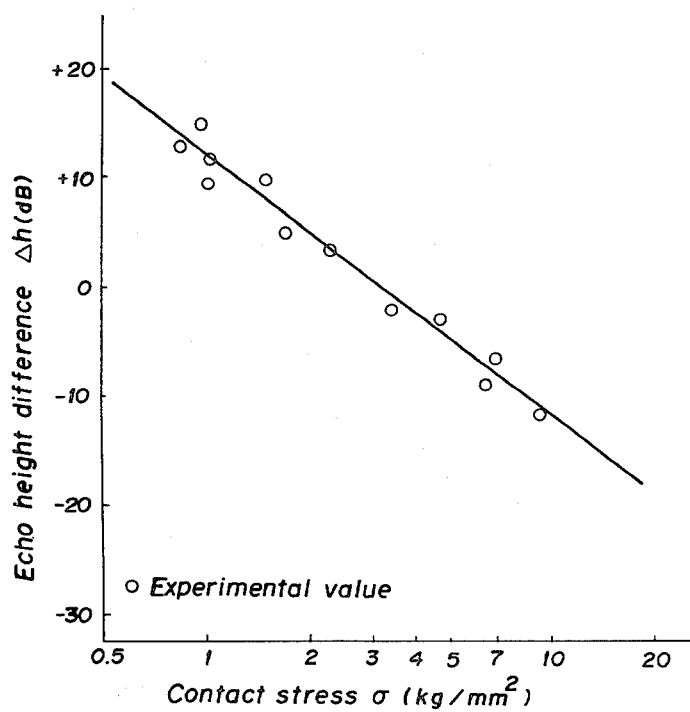
FIG. 16 is a graph showing the relationship between the contact stress obtained by the method shown in FIG. 12 and the comparative value of the echo height.

Also, the relationship between the contact stress $\sigma$ and the echo height difference which are obtained by the measurement method of FIG. 12 (using a boss and a bushing identical with those providing the graph shown in FIG. 10), is illustrated by small circles plotted in FIG. 16. These plotted circles were subjected to said least square method to provide such rectilinear line as shown in FIG. 16.

Figure 17:
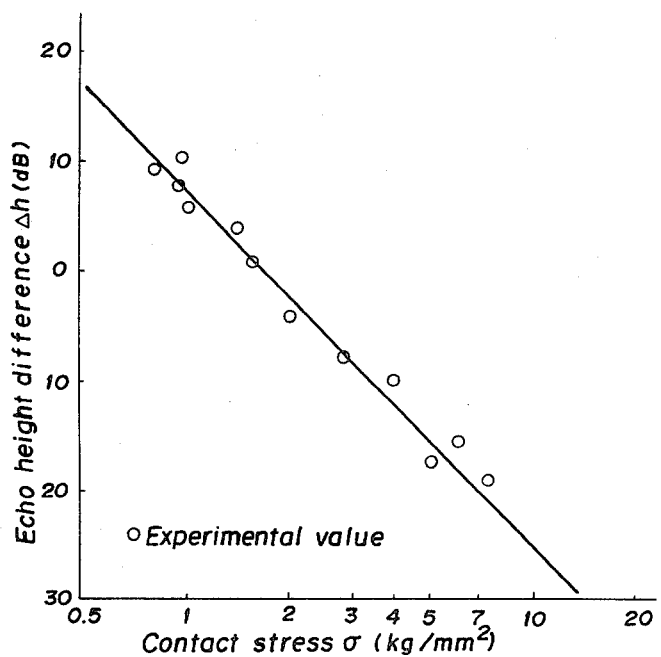
FIG. 17 is a graph showing the relationship between the contact stress obtained by the method shown in FIG. 13 and the comparative value of the echo height.

Also, the relationship between the contact stress $\sigma$ and the echo height difference (similar to that mentioned above) which are obtained by the measurement method shown in FIG. 13 is illustrated by the small circles plotted in FIG. 17. By relying on the least square method, they provide the rectilinear line as shown in FIG. 17.

Figure 18:
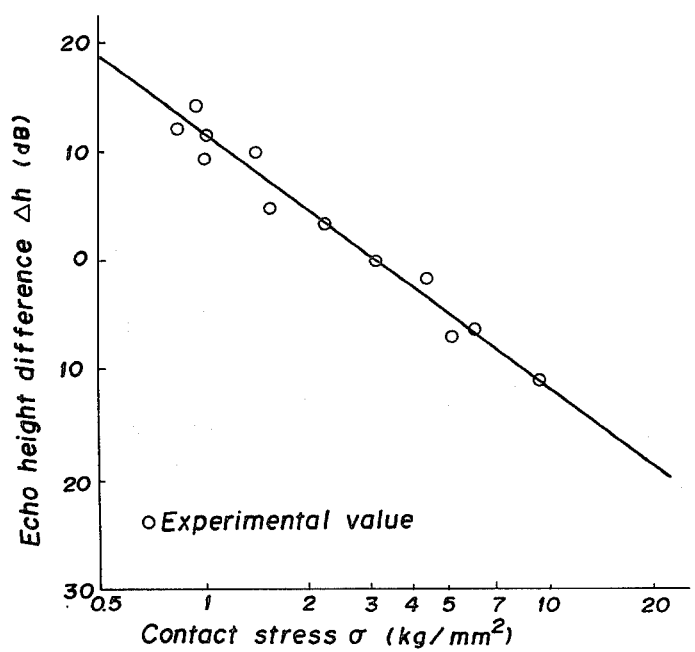
FIG. 18 is a graph showing an example of the relationship between the contact stress obtained by the method shown in FIG. 14 and the comparative value of the echo height.

Furthermore, the relationship between the contact stress $\sigma$ and the echo height difference (similar to that shown above) which are obtained by the measurement method shown in FIG. 14 is illustrated by the small circles plotted in FIG. 18. By relying on the least square method, they provide the rectilinear line shown in FIG. 18.

By comparing FIG. 17 with FIG. 10, it is apparent that by tilting one of regression lines it becomes substantially identical with the other. This is due to the fact that the number of times the $P_1$ echo passes through the contacting surfaces is the same in the method illustrated in FIG. 6 and the method illustrated in FIG. 13. It should be noted, however, that the regression formula is slightly different in the instance of FIG. 17 and the instance of FIG. 10. This is because of the fact that, according to the method illustrated in FIG. 13, an average contact stress at the site a and the site b of the contacting surfaces is intended to be measured. Also, the variance of the experimental values relative to the regression line of FIG. 17 is noted to be substantially the same as in FIG. 10. Furthermore, the comparison indicates that the accuracy of measurement also is of a similar level to that obtained in accordance with the method illustrated in FIG. 6.

Now, FIGS. 16 and 18 are compared with FIGS. 10 and 17. It will be noted that, in the case of FIGS. 16 and 18, the tilt of the regression line is somewhat gentler than that of FIGS. 10 and 17. This is due to the fact that, while in the instance of FIGS. 6 and 13, the $P_1$ echo represents an acoustic pressure of a wave which has been transmitted through the contacting surfaces twice, the instance shown in FIGS. 12 and 14 is such that the $P_1$ echo represents an acoustic pressure of a wave which has been transmitted through the contacting surfaces only once. However, as will be apparent from FIGS. 16 and 18, the regression lines have a sufficient tilt to allow a quantitative evaluation, and also the variance of the experimental values for the regression lines is of a substantially the same level with that of FIG. 10. It will thus be understood that the accuracy of measurement in these instances shown in FIGS. 16 and 18 is almost in the same level as for FIG. 10.

Figure 19:
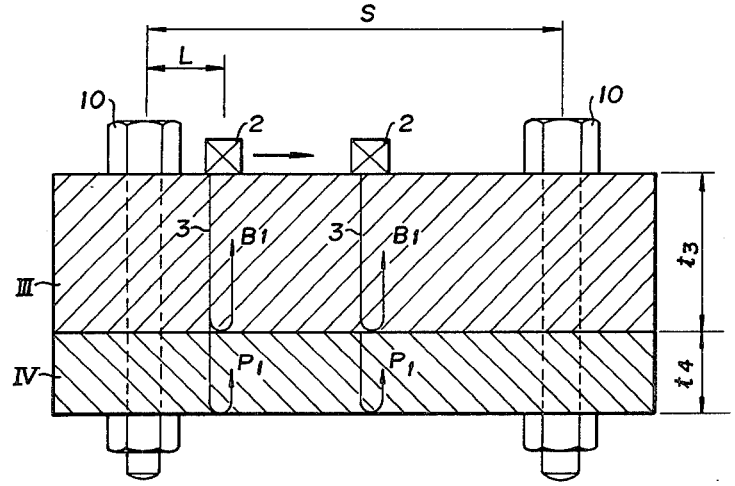
Figure 20:
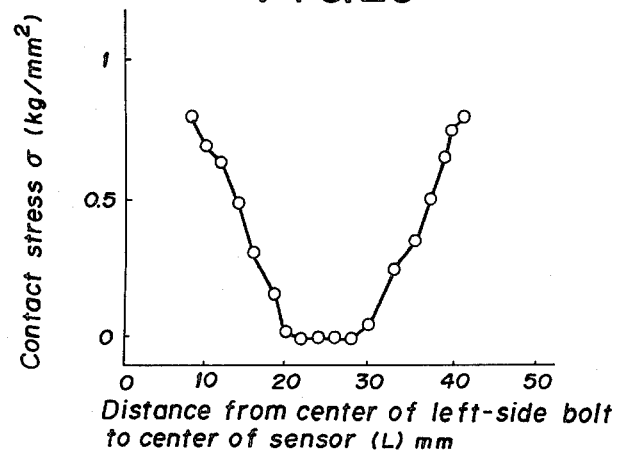

FIGS. 19 and 20 show an instance wherein the present invention is applied to the measurement of the contact stress at bolt-fastened surfaces. More particularly, the state in which a plate III made of a carbon steel for machine structural use which is labeled S45C (plate thickness $t_3 = 36$ mm) and another plate IV made of the same material (plate thickness $t_4 = 14$ mm) are fastened together by two bolts 10 having a diameter of 8 mm, is shown in FIG. 19. In FIG. 19, the distance S between these two bolts 10 is 50 mm, and the fastening strength is 600 kgf. The transducer 2 which is used in the measurement is identical with that used in the instance of FIG. 6. The transducer 2 is moved at pitches of about 2 mm from the right side face of the left-side bolt in the drawing up to the left side face of the right-side bolt on a line extending between the central axes of these two bolts, and in the manner identical to that shown in FIG. 6, the contact stress of the contacting surfaces is measured.

Let us here assume that the distance from the central axis of the left side bolt 10 up to the center of the transducer 2 is designated as L, and the distribution of the contact stress $\sigma$ obtained from this measurement is shown in FIG. 20. The result shows that, when L is between about 20 mm and 30 mm (meaning the instance that the distance between the two bolts 10 is 50 mm and said L indicates the central range of about 10 mm between the two bolts 10), the contact stress becomes almost nil, and it will be noted that the contact stress shows a bathtub shaped curve with the left-side and the right-side curves being substantially symmetrical.

The foregoing respective embodiments show invariably the instances wherein an ultrasonic wave transducer is applied directly onto the surface of at least one of the two metal masses which are united together. The present invention, however, is not limited to such embodiment.

As a modified embodiment, the present invention is able to display other specific effects by arrangements in which both the ultrasonic wave transducer and the object for measurement are immersed in a liquid in such a state that there is provided a certain distance between the sensor and the object, and that an ultrasonic wave is caused to impinge onto the contacting surfaces of the solid masses of the object via said liquid, i.e. by relying on the so-called liquid immersion method.

Description will hereunder be made of a concrete embodiment in which the present invention incorporates to the liquid immersion method.

Figure 21:
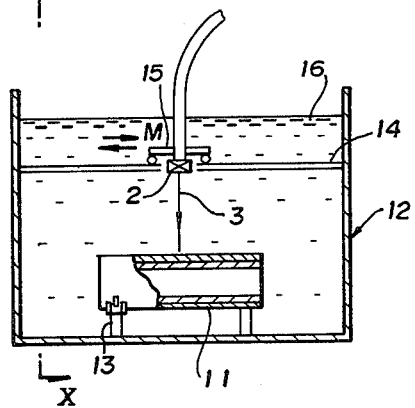
FIG. 21 is a diagrammatic vertical sectional view showing the method of continuous measurements of an contact stress at contacting surfaces of object via a liquid.
Figure 22:
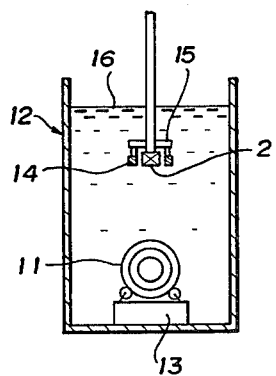
FIG. 22 is a sectional view taken along the line X—X in FIG. 21.

FIGS. 21 and 22 show the method wherein an object 11 for measurement which comprises a boss and a bushing is supported rotatably in a liquid vessel 12. In this embodiment use is made of the good transmissibility of the longitudinal ultrasonic wave through a liquid, to carry out a measurement continuously and without contact of the transducer with the object. More particularly, in FIGS. 21 and 22, numeral 13 represents a supporting pedestal for rotatably supporting an object 11 for measurement in the bottom portion of the liquid vessel 12. The object 11 is supported on this supporting pedestal 13. A guide rail 14 is provided to span the upper portion within the liquid vessel 12. A carrier 15 carrying the ultrasonic wave transducer 2 on said guide rail is arranged so as to be movable in parallel with the axis of the object. The interior of the vessel 12 is filled with a liquid 16 which may be oil or water. While either by gently rotating the object 11 or keeping it stationary, the carrier 15 is moved in the direction of the arrow M, to thereby be able to continuously measure the contact stress at the contacting surfaces of the object throughout the entire circumference and the entire length thereof.

Figure 23:
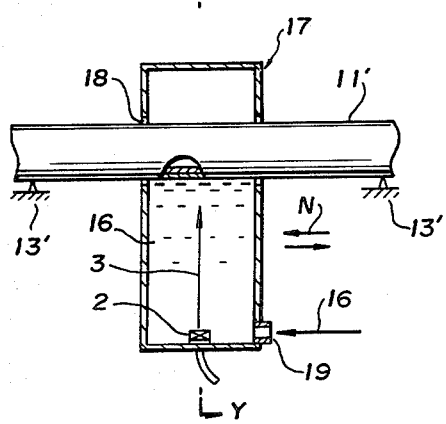
Figure 24:
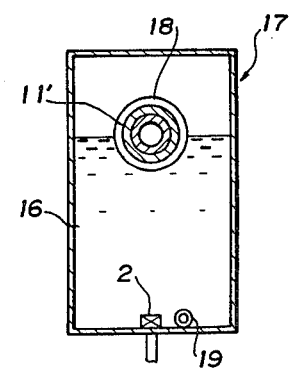

Also, FIGS. 23 and 24 illustrate the embodiment of the method of making a non-contacting and continuous measurement in case the object 11' is of such a large size that its whole length cannot be contained in the liquid vessel. In this embodiment, the walls on both upper sides of the liquid vessel 17 are provided with a hole 18 of such size as to allow the free insertion therethrough of the object 11'. Also, a hole 19 for supplying the liquid 16 is provided in the lower portion of the vessel. Furthermore, an ultrasonic wave sensor 2 is attached to the bottom of the vessel 17 so as to face upwardly. The object 11' is inserted through the hole 18, and this object 11' is rotatably supported by a supporting pedestal 13' at both sides of the vessel 17 externally thereof. A liquid 16 which may be either oil or water is continuously supplied through the supply hole 19 into the vessel 17, and this liquid 16 is caused to overflow through the hole 18, to thereby keep both the object 11' and the ultrasonic wave transducer 2 immersed in the liquid 16. Either the vessel 17 or the object 11' is moved in the direction of the arrow N, to thereby be able to make a measurement continuously along the entire circumference and also longitudinally thereof.

According to the methods shown in FIGS. 21 through 24, it will be noted that these methods are suitable for an automated measurement, along the entire circumference and the entire length, of a cylindrical object such as a boss and a bushing.

As will be apparent from the foregoing description, according to the liquid immersion method, it is not necessary to make a measurement by applying an ultrasonic wave transducer directly onto an object for measurement. Thus, this method permits anybody to easily make an accurate and stable quantitative measurement without being subjected to any effect arising from the manner of application of the transducer or from the nature of the site at which the transducer is applied.

As a further important advantage, it may be said that this liquid immersion method permits one to provide an appropriate necessary distance between the ultrasonic wave transducer and the object in accordance with the nature (such as dimension and configuration) of the object. Accordingly, this method can be applied also in such an instance wherein the object has a very small diameter, or wherein the object has a very small thickness, and yet an effect similar to that of the foregoing embodiments can be obtained.

Figure 6:
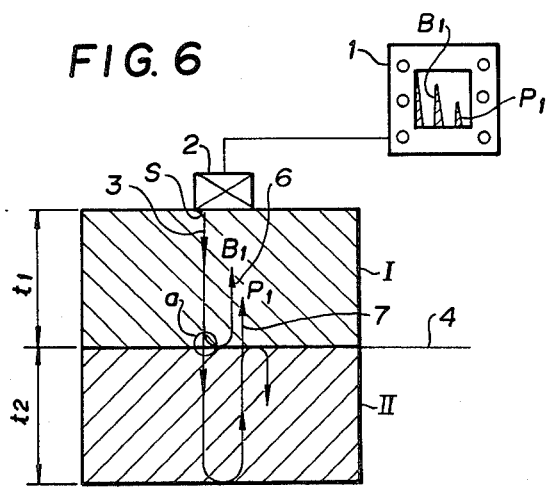
FIG. 6 is a brief explanatory illustration showing an example of an application of the present invention to the measurement of the contact stress of the boss and the abutting bushing shown in FIG. 5.
Figure 25:
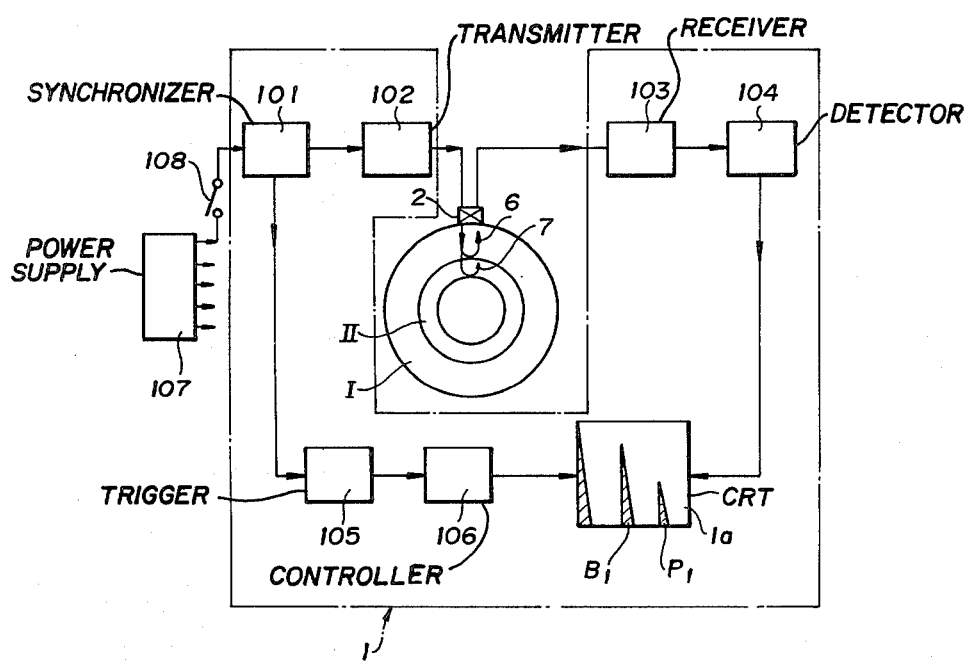
Figure 26:
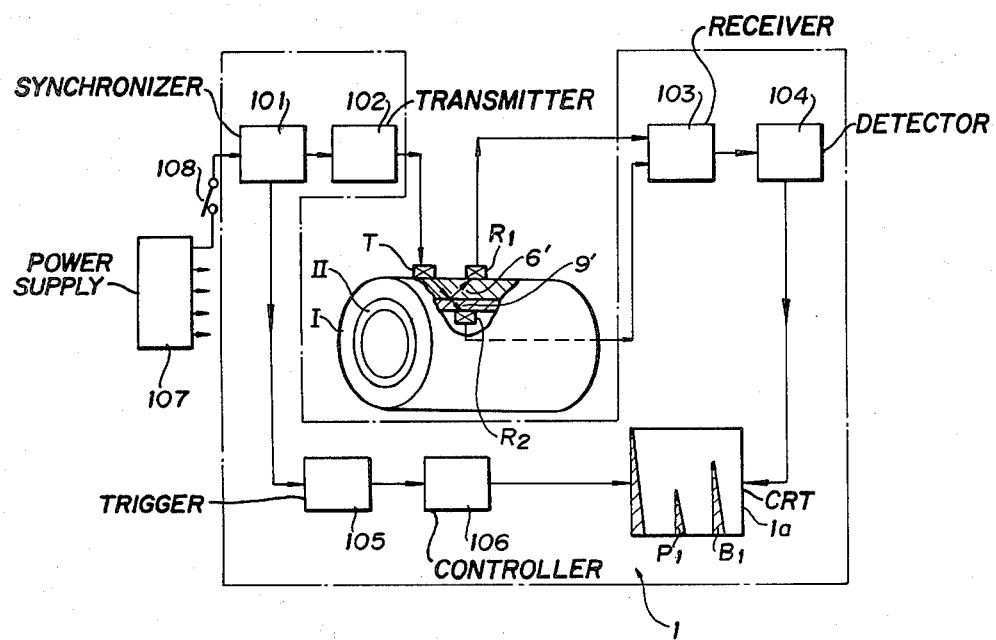

FIGS. 25 and 26 are explanatory illustrations respectively showing how the methods illustrated in FIGS. 6 and 14 can be carried out by using a known ultrasonic flaw detector of pulse echo type 1.

In FIGS. 25 and 26, numeral 101 denotes a synchronizing section (synchronizer) for generating a single voltage intended to impart a timewise limitation to the respective circuits in the ultrasonic flaw detector 1. Numeral 102 denotes a signal transmitting section (transmitter) for receiving a signal voltage from said synchronizing section 101 and for applying a pulse signal to either the ultrasonic wave transducer 2 or T. Numeral 103 denotes a signal receiving section (receiver) for receiving an electric signal from said ultrasonic wave transducer 2 or $R_1$, $R_2$ and for amplifying this signal up to several 10 decibels and for transmitting this amplified signal to a detecting section (detector) 104. The detecting section 104 is one which rectifies the high frequency output supplied from the signal receiving section 103 for deriving a DC voltage signal used as the vertical deflection signal for the CRT. Numeral 105 denotes a triggering section (trigger) for delaying somewhat the timing of generation of the triangular wave on the time axis (horizontal axis) relative to the timing of the synchronous signal coming from the synchronizing section 101, and this section is used for such purposes as displaying only the vicinity of the measurement spot on the CRT, or for establishing the coincidence between the origin of the distance of the beam path with the zero point on the graduation of the CRT at the time of an incidence of a wave at a tilted angle. Numeral 106 denotes a time control section (controller) for forming a voltage intended for moving the bright spot on the CRT horizontally at a constant speed. Numeral 107 denotes a power supply, and numeral 108 denotes a switch.

Next, description will be made of an echo display on a CRT obtained by using a ultrasonic flaw detector of pulse echo type 1 having the above-described arrangement.

As a first step, the synchronizing section 101 is connected to the power supply 107, whereupon the synchronizing section 101 generates a signal voltage for causing the signal transmitting section 102 to generate a high frequency pulse having a correct time interval. The signal transmitting section 102, in accordance with the timing command received from the synchronizing section 101, applies a high frequency pulse to either the ultrasonic wave transducer 2 or T through a high frequency cable. The high frequency pulse applied to either the transducer 2 or T is converted to an ultrasonic wave in accordance with the magnitude of the voltage of the pulse, and then it is transmitted to the object where surface contact stress is to be measured.

The acoustic pressure of the ultrasonic wave reflected from the contacting surfaces of the object and the acoustic pressure of the ultrasonic wave which has been transmitted through the contacting surfaces are again converted to voltages by either the transducer 2 or transducer sensors $R_1$ and $R_2$, and they are transmitted to the signal receiving section 103 through the high frequency cable. At the signal receiving section 103, these voltages are amplified, and the resulting voltages are transmitted to the detecting section 104 to be converted to a DC waveshape from the AC waveshape.

On the other hand, the synchronizing section 101, concurrently with its outputting of a signal to said signal transmitting section, outputs a signal to the time control section 106 via the trigger delaying section 105. Also, the time control section 106 generates a voltage for moving the bright spot on the CRT horizontally at a constant speed.

In this way, by applying a signal voltage supplied from the detecting section 104 and also a triggering voltage supplied from the time control section 106 to the CRT, the signal voltage coming from the detecting section 104 is deflected by a vertical deflecting plate, and also the triggering voltage coming from the time control section 106 is deflected by a horizontal deflecting plate, so that the $B_1$ echo and the $P_1$ echo are displayed on the graduation screen 1a provided on the foreground of the CRT.

The method described above represents a method of making a visual measurement by the display of echoes on the CRT. It should be noted, however, that in place of making display on the CRT, it is also possible to digitalize the analog amounts of echo heights by a usually practiced means, and to compute the ratio of these analog amounts to thereby exhibit these values in digitalized form. Also, still further, these values may be stored in a memory, so that by making a comparison of these values with a reference value, a disorder of the machine may be detected, or such memory may be utilized in effecting automatic control.

Though needless to say, it is a matter of course that the present invention is not limited to the above-described preferred embodiments alone, but is may be modified in various ways within the scope of the technical conception of the present invention.

We claim:

1. A method of measuring contact stress, comprising the steps of:
   (1) causing an ultrasonic wave to impinge upon the contacting surfaces of first and second abutting masses of an object;
   (2) detecting the relative amplitudes of acoustic pressure of a first portion of the wave which is reflected by the contacting surfaces, and of a second portion of the wave, which is transmitted through the contacting surfaces, relative to one another; and
   (3) determining the contact stress at the contact surfaces, said contact stress being a function of the relative amplitudes of acoustic pressure of the first and second portions of the wave.

2. A method as in claim 1, wherein said detecting step includes the step of detecting the ratio of the relative amplitude of acoustic pressure of the first portion of the wave to the relative amplitude of acoustic pressure of the second portion of the wave.

3. A method as in claim 1, wherein said step of causing comprises the step of directing the wave toward the contacting surfaces from a first exposed surface of the first mass on one side of the contacting surfaces; and said step of detecting comprises the steps of detecting the amplitude of acoustic pressure of the first portion, externally of the first exposed surface, and detecting the amplitude of acoustic pressure of the second portion, externally of a second exposed surface of the second mass on the other side of said contacting surfaces.

4. A method as in claim 3, wherein said step of causing comprises the step of causing with a first transducer the ultrasonic wave to be transmitted to the contacting surfaces so as to impinge normally thereon and so that the first portion is reflected normally back to the first transducer and the second portion is transmitted normally toward the second exposed surface, said detecting step including the concurrent steps of detecting the amplitude of acoustic pressure of the first portion with the first transducer and detecting the amplitude of acoustic pressure of the second portion with a second transducer at the other side of the contacting surfaces.

5. A method as in claim 3, wherein said step of causing includes the step of causing the ultrasonic wave to impinge on the contacting surfaces at an oblique angle so that the first portion is reflected from the contacting surfaces at an oblique angle and the second portion is transmitted through the contacting surfaces at a non-normal angle to the contacting surfaces.

6. A method as in claim 1, wherein said step of causing comprises the step of directing the wave toward the contacting surfaces from a first exposed surface of said first mass on one side of the contacting surfaces; and said step of detecting comprises the steps of detecting externally of the first exposed surface the amplitude of acoustic pressure of one portion of the wave which is reflected by the contacting surfaces, and detecting externally of the first exposed surface the amplitude of acoustic pressure of an other portion of the wave which is in turn transmitted through the contacting surfaces, reflected by a second exposed surface of the second mass on the other side of the contacting surfaces toward the contacting surfaces and again transmitted through the contacting surfaces to the first exposed surface.

7. A method as in claim 6, wherein said step of causing comprises the step of causing, with an impinging transducer at said one side, the ultrasonic wave to be directed to the contacting surfaces so as to impinge normally thereon and so that the one portion is reflected normally back to the impinging transducer and the other portion is transmitted normally toward the second exposed surface, the detecting step including the steps of receiving the one and the other portions at the impinging transducer, and detecting the relative amplitudes of acoustic pressures of the one portion of the other portion, relative to one another.

8. A method as in claim 6, wherein said step of causing comprises the step of causing the ultrasonic wave to impinge on the contacting surfaces at an oblique angle so that the one portion is reflected from the contacting surfaces at an oblique angle and the other portion is transmitted through the contacting surfaces at a non-normal angle to the contacting surfaces.

9. A method as in claim 1, further comprising the step of immersing an ultrasonic wave transducer and the object in a liquid with the object spaced from the transducer, said step of causing comprising the step of directing the ultrasonic wave from said transducer onto the contacting surfaces via said liquid.

10. A method as in claim 9, further comprising the steps of: providing a vessel filled with a liquid; rotatably supporting a cylindrical object having cylindrical contacting surfaces whose contact stress is to be measured, at the bottom of the vessel; arranging the ultrasonic wave transducer in the upper part of the vessel so as to be movable parallel to the rotational axis of the cylindrical object; and continuously and simultaneously rotating the cylindrical object about its rotational axis and moving the ultrasonic transducer parallel to the rotational axis, during said detecting step; said detecting step including the steps of continuously detecting the relative amplitudes of acoustic pressure of the first and second portions with the ultrasonic transducer while the cylindrical object is rotating and the ultrasonic transducer is moving; said determining step including the step of continuously determining the contact stress along the entire length and circumference of the object while the cylindrical object is rotating and the ultrasonic transducer is moving, the contact stress being a function of said relative amplitudes.

11. A method as in claim 9, further comprising the steps of providing a liquid vessel; forming holes in opposing side walls of the vessel; inserting a cylindrical object having cylindrical contact surfaces whose contact stress is to be measured, in the opposing holes for rotation therein; rotatably supporting the cylindrical object in the holes for rotation about its rotational axis; continuously supplying a liquid into the vessel while the liquid overflows through the holes with the object inserted in the holes; and continuously rotating the object about its rotational axis and moving the object axially relative to the vessel during said detecting step; said step of causing including the step of causing ultrasonic waves to continuously impinge onto the contacting surfaces via the liquid during the continuously rotating and moving step; said detecting step including the step of continuously detecting the relative amplitudes of acoustic pressure of the first and second portions while the cylindrical object is rotating about its rotational axis and moving axially relative to the vessel; said determining step including the step of continuously determining the contact stress along the entire length and circumference of the cylindrical object while the cylindrical object is rotating about its rotational axis and moving axially relative to the vessel, said contact stress being a function of said relative amplitudes.

* * * * *